(12) United States Patent  
Simpson

(10) Patent No.: US 6,494,961 B2  
(45) Date of Patent: Dec. 17, 2002

(54) METHOD OF CONTROLLING SOLUTION CONCENTRATION IN STRIP CLEANING LINE

(75) Inventor: Stephen D. Simpson, Kingston (CA)

(73) Assignee: Alcan International Limited, Montreal (CA)

(*) Notice: Subject to any disclaimer, the term of this patent is extended or adjusted under 35 U.S.C. 154(b) by 0 days.

(21) Appl. No.: 09/823,672

(22) Filed: Mar. 30, 2001

(65) Prior Publication Data

US 2002/0139397 A1 Oct. 3, 2002

(51) Int. Cl.[7] .............................. B08B 3/00; B08B 3/08; C23G 1/02
(52) U.S. Cl. ................. 134/3; 134/15; 134/18; 134/28; 134/29; 134/32; 134/36; 134/41
(58) Field of Search ................. 134/3, 15, 18, 134/28, 29, 32, 36, 41

(56) References Cited

U.S. PATENT DOCUMENTS

| | | | |
|---|---|---|---|
| 4,851,148 A | 7/1989 | Yamasoe et al. | 252/142 |
| 5,175,502 A | 12/1992 | Rodabaugh et al. | 324/439 |
| 5,472,516 A | * 12/1995 | Hanson et al. | 134/18 |
| 5,803,984 A | * 9/1998 | Lordo et al. | 134/18 |
| 6,033,485 A | * 3/2000 | Didier et al. | 134/3 |

FOREIGN PATENT DOCUMENTS

| | | |
|---|---|---|
| EP | WO 00/33061 | 6/2000 |
| JP | H7-54175 | 2/1995 |

* cited by examiner

Primary Examiner—Zeinab El-Arini  
(74) Attorney, Agent, or Firm—Cooper & Dunham LLP

(57) ABSTRACT

An automatic control system is provided for acid concentration in an aluminum strip cleaning line wherein an aluminum strip is contacted with an acid solution while passing through an acid cleaning bath and the concentration of the acid in the bath is adjusted by adding either concentrated acid or water to the bath. A conductivity probe is provided in the acid bath and generates a first signal approximately proportional to the free acid concentration of the bath. An on-line process titrator periodically samples the acid bath and by a dual endpoint titration obtains the free acid concentration and total acid concentration of the bath and thereby generates a second signal indicative of the actual free acid concentration and the total acid concentration. These first and second signals are fed to a programmable logic controller, which based on the signal from the titrator calculates a correction factor for the signal from the conductivity probe to thereby obtain a corrected value for free acid concentration. The bath acid concentration is then adjusted as required based on the corrected specific conductivity value. The above procedure may also be used in the cleaning of an aluminum strip with an alkali solution.

7 Claims, 2 Drawing Sheets

METHOD OF CONTROLLING SOLUTION CONCENTRATION IN STRIP CLEANING LINE

BACKGROUND OF THE INVENTION

This invention relates a method of automatically controlling chemical concentration in a metal strip cleaning line, particularly an aluminum strip cleaning line.

In the processing of aluminum strip, e.g. for use in automotive production, it is necessary to clean the surfaces of the strip material. One way of doing this is by passing the strip material on a continuous basis through a cleaning line which includes an acid wash section or sections(s), followed by a rinse section or sections. In each section acid solution or rinse water respectively is sprayed via nozzles onto the top and bottom faces of the strip passing through the line. The sprayed liquid is collected in tanks at the bottom of the enclosure from where it is re-circulated by pumps back through the nozzles.

In this procedure it is important to control the free acid strength in the wash section(s), and this is typically done by providing a conductivity probe immersed in the fluid in the bath. A specific conductivity signal which varies approximately in proportion to the free acid concentration of the solution is typically provided by the conductivity probe and this is used to adjust the acid concentration. However, use of the specific conductivity signal to estimate the free acid concentration is prone to offset errors due to impurities, and temperature fluctuations in the bath which increase or decrease the actual specific conductivity of the cleaning solution independently of free acid concentration, and errors due to drift of the conductivity probe itself caused by build up on the electrode.

Because of this unreliability, it is the usual practice to periodically perform manual titrations to verify that the concentration is still within limits. If a discrepancy is found, options are manual recalibration of the probe or manual adjustment of the bath using trial and error methods. This requires skilled technicians and/or operators, is labour intensive and is subject to operator errors in the calibration and correction. It has been found that the bath concentration can experience considerable drift from target before a correction is made, resulting in product which is improperly processed.

In making the above corrections, the objective is to control the free acid concentration (FAC) in the bath, which is the acid available for reaction with the aluminum surface as opposed to the total acid concentration (TAC). The total acid concentration comprises the free acid concentration plus soluable reaction products. Control of the free acid concentration is done by estimating the free acid concentration and adding fresh concentrated acid from a storage tank or water depending on whether the free acid is too low or too high.

Japanese Patent Publication JP 7-54175, published Feb. 28, 1995 describes a method of controlling acid concentration in a steel pickling line by monitoring weight loss. However, it is not concerned with the problems related to a cleaning line and the importance of the correctness of the free acid concentration.

It is also known to clean metal strips by passing the strip through a cleaning line where an alkali solution is used rather than an acid solution. An example of this can be found in Japanese Patent Publication JP 11-269,678, published Oct. 5, 1999, where an alkali solution was used to degrease and clean cold-rolled steel strips. When cleaning with alkali solution, the same problems in controlling concentration are encountered as described above for acid cleaning solutions.

It is the object of the present invention an automated and more accurate method of controlling the chemical concentration in a metal strip cleaning line.

SUMMARY OF THE INVENTION

One embodiment of this invention relates to a method for automatically controlling acid concentration in an aluminum strip cleaning line in which an aluminum strip is contacted with an acid solution while passing through a cleaning bath and the concentration of the acid in the bath is adjusted by adding either concentrated acid or water to the bath. A conductivity probe is provided in the acid cleaning bath and this probe generates a first signal approximately proportional to the free acid concentration of the bath. An on-line process titrator is also provided to periodically sample the acid bath and by a dual endpoint titration, obtain the free acid and total acid concentration of the bath. The on-line titrator generates a second signal indicative of the actual free acid concentration and the total acid concentration. The above signals are fed to a programmable logic controller (PLC) which, based on the signal from the titrator, calculates a correction factor for the signal from the conductivity probe to thereby obtain a corrected specific conductivity value proportional to the free acid concentration. Based on this corrected value, the bath acid concentration is automatically and continuously adjusted as required based on the corrected specific conductivity value. The acid used for this purpose is typically sulfuric acid. The difference between the total and free acid concentration is indicative of the level of bath contaminants and can therefore be used to adjust the amount of metered overflow from the wash section.

The conductivity probe measures the ability of a solution to conduct an electric current between two electrodes. An increase in concentration of ions in the solution results in higher conductivity values. Conduction is measured in Siemens (formerly known as mho) and the conductivity probe can also be used to find the concentration of total dissolved solids in a sample of water.

A new titration is conducted automatically at timed intervals or when requested by the PLC and the value of the specific conductivity at the time of the titrator sample being drawn is stored in the PLC memory. The titration timer is reset to zero after each successfully completed titration.

The titrator free acid titration % input validation is accomplished as follows. If the difference between the new value of free acid and the recorded value of free acid is more than x percent of the current value, the current value is retained and a new titration is requested by the PLC. A warning signal is sent to the operator station advising "Acid Concentration out of Range—Rechecking Concentration". This is to ensure that any large discrepancies are not due to a titration error or anomaly. The value of the next titration is accepted by the PLC and replaces the current value.

Immediately upon receiving a valid reading of free acid from the titrator input, a Conductivity Correction Factor is calculated and stored in the PLC. The calculation is as follows:

Conductivity Correction Factor=Free acid Titration % −{Specific conductivity ($\mu$Siemens/cm)*Concentration Factor (1/$\mu$Siemens/cm)}

The Concentration Factor is the conversion factor for specific conductivity to Free Acid % with units 1/$\mu$Siemens/cm which is determined once for each type of cleaning solution by an off-line calibration. The true acid concentration based on the output of the conductivity meter is determined in the PLC by the following algorithm:

Conductivity Corrected Free Acid Concentration %={Specific Conductivity (µSiemens/cm)*Concentration Factor (1/µSiemens/cm)}+Conductivity Correction Factor A value indicative of the level of bath contamination is also calculated in the PLC as follows:

Contaminant Level=Total acid Titration %−Free acid Titration %

The acid cleaning bath is typically followed by one or more rinsing sections where the acid cleaned strip is thoroughly rinsed. The cleaning and rinsing liquids are preferably sprayed on the strip material by means of a plurality of spray nozzles above and below the strip. These are connected to pumps to simultaneously spray the top and bottom faces of the moving strip. The cleaning and rinsing liquids flow back down into a reservoir in each section to be re-circulated through the nozzles.

In a further embodiment of the invention, the acid cleaning bath in the above description may be replaced by an alkali cleaning bath. The same procedures as described above are then used to control the alkali concentration in the cleaning bath.

The method of this invention has the important advantage of requiring no skilled technicians or operators and allowing more precise control of the process by semi-continuously compensating for measurement errors.

BRIEF DESCRIPTION OF THE DRAWINGS

In the drawings which illustrate certain preferred embodiments of this invention.

DETAILED DESCRIPTION OF THE INVENTION

Figure 1:
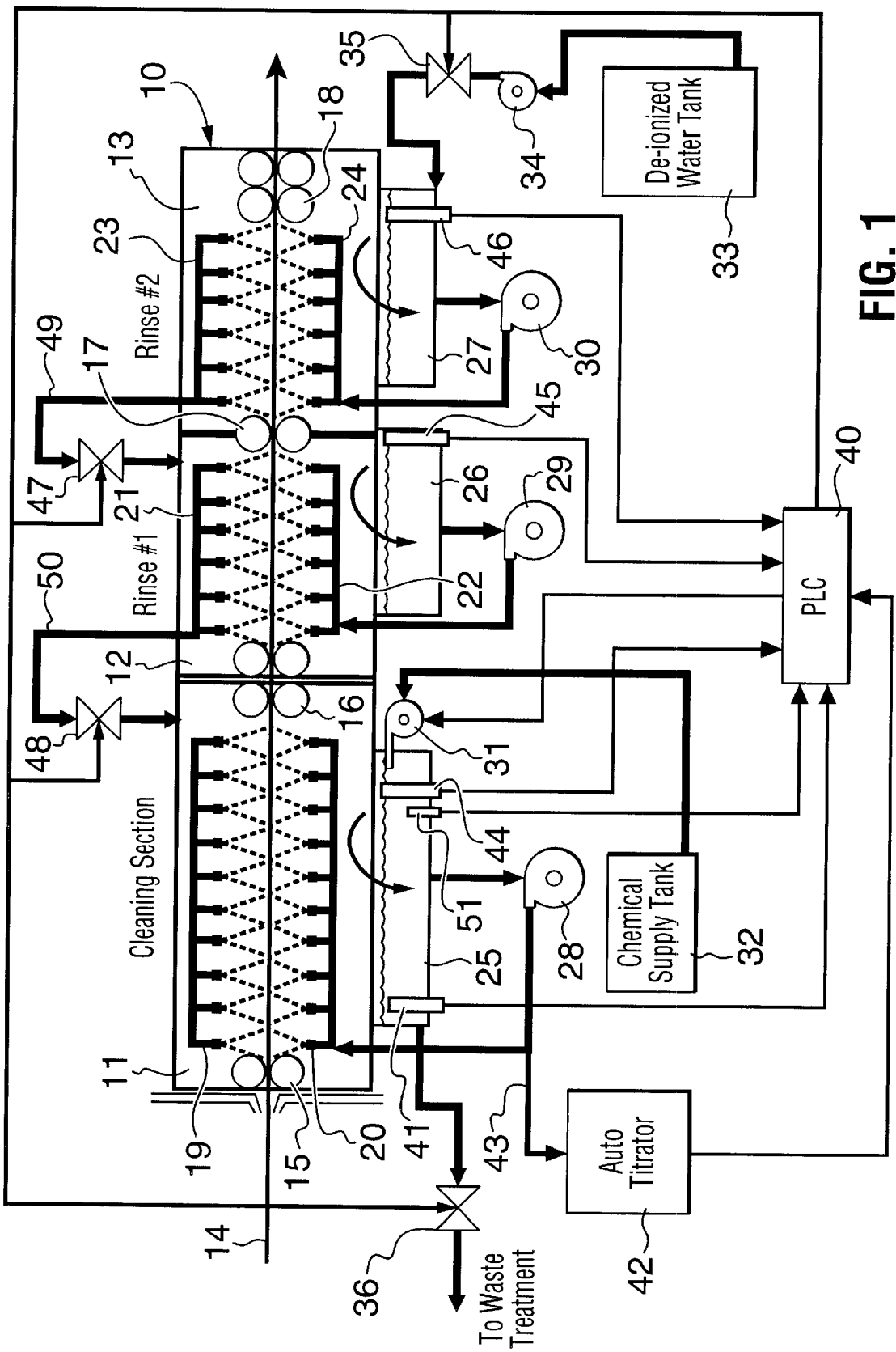
FIG. 1 is a schematic view in partial section of a strip cleaning line according to the invention.

A typical acid cleaning line for aluminum sheet used in the automotive industry is shown in FIG. 1. The cleaning line 10 consists of three sections, namely an acid cleaning section 11, a first rinse section 12 and a second rinse section 13. In the acid cleaning section 11, acid solution is sprayed through nozzles 19 and 20 onto the top and bottom faces respectively of an aluminum sheet 14. From acid cleaning section 11, the aluminum strip passes through a first rinse section 12 where rinse water is sprayed on the top and bottom of the strip via upper and lower spray nozzles 21 and 22 and from there through the second rinse section 13 where further rinse water is sprayed on the top and bottom of the strip via upper and lower spray nozzles 23 and 24.

A series of squeegee rolls are used including an inlet pair of rolls 15, a double pair of rolls 16 between the acid cleaning section 11 and the first rinse section 12, a further pair of rolls 17 between the two rinse sections 12 and 13 and finally a double pair of rolls 18 at the exit end from the second rinse 13.

Tanks or reservoirs 25, 26 and 27 are located beneath the spray nozzles of cleaning sections 11 and rinse sections 12 and 13 respectively to collect and re-circulate the fluid from each section. The fluid re-circulation is by way of pumps 28, 29 and 30, each of which is provided with a bypass line (not shown) which provides re-circulation of fluid when the supply line to the nozzles is closed. Back flow between adjacent tanks 25, 26 and 27 is through servo-valves 47 and 48 which are connected via lines 49 and 50 respectively to fluid feed pumps for the spray nozzles of rinse sections 12 and 13. Thus, make-up water required by cleaning section 11 is supplied through servo-valve 48 from rinse section 12, which is in turn replenished through servo-valve 47 from rinse section 13. Replenishing of rinse section 13 is from de-ionized water supply tank 33 via pump 34 and servo-valve 35. Fresh acid is supplied from supply tank 32 via pump 31 into cleaning section tank 25. A constant overflow from the cleaning section 11 to waste is maintained by bleeding out fluid at a controlled rate through servo-valve 36 to flush out contaminants. The overflow rate required is determined with reference to the difference between the total acid and free acid concentration in the bath as determined by the automatic titrator, the larger this value the greater the level of contaminants. A reduction of contaminants, if required, is effected by increasing the overflow rate from the wash section to waste. There is also an overflow weir to waste (not shown) in each of tanks 25, 26 and 27 for the situation where the fluid level becomes too high in one or more of the tanks.

The system is controlled by programmable logic controller (PLC) 40, which receives signals from fluid level sensors 44, 45 and 46 in tanks 25, 26 and 27 respectively, as well as from conductivity probe 41 in tank 25 and from on-line titrator 42. The titrator 42 receives acid cleaning fluid via line 43 from the fluid being re-circulated by pump 28.

Signals from PLC 40 go out to control waste servo-valve 36, rinse water back flow servo-valves 47 and 48, fresh input water servo-valve 35 and acid feed pump 31.

Figure 2:
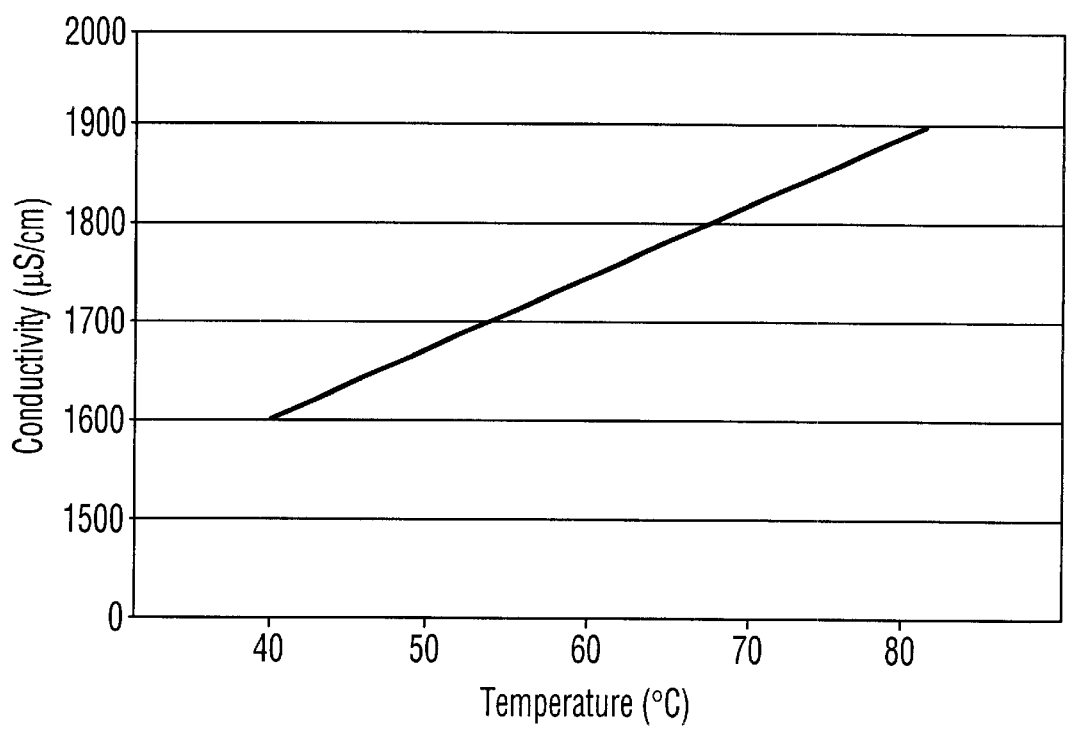
FIG. 2 is a plot showing the effect of temperature on specific conductivity.
Figure 3:
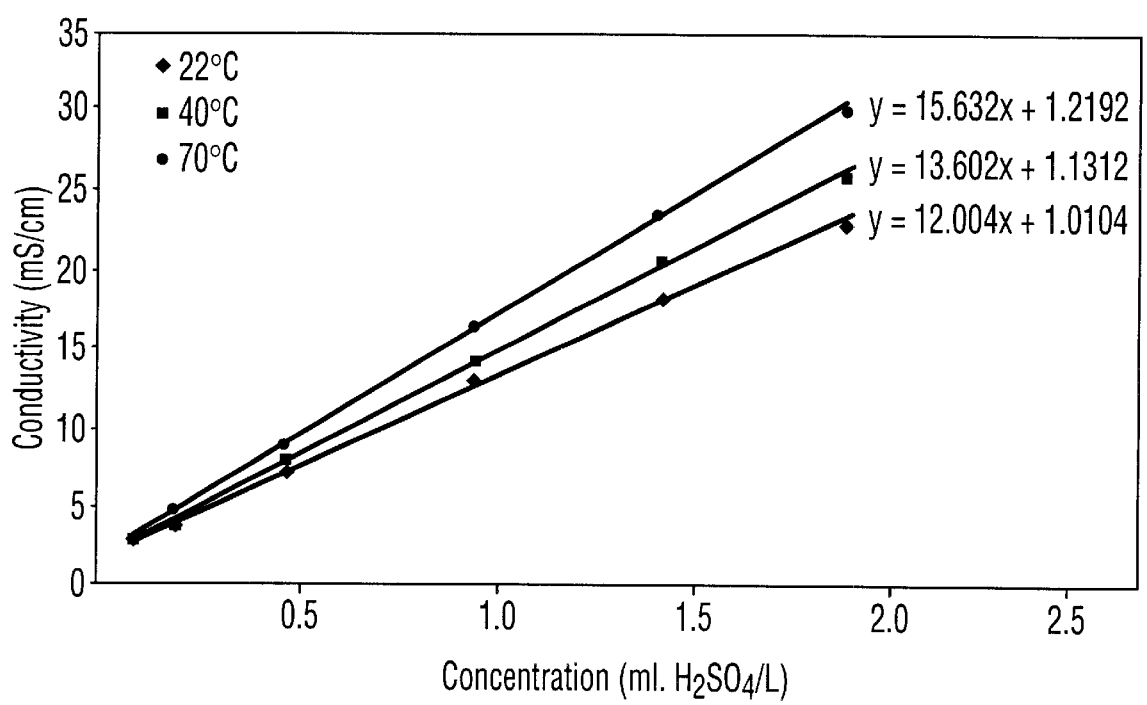
FIG. 3 is a plot showing the effect of acid concentration on specific conductivity as a function of temperature.

The specific conductivity varies with temperature and this has an approximately straight line relationship as shown in FIG. 2. The PLC 40 monitors the temperature in acid cleaning tank 25 via thermocouple 51 and a temperature normalization factor is applied to the conductivity signal from probe 41. Some commercially available probes are supplied with built-in temperature compensation in which case the line PLC normalization factor may be set to a value of 1. The effect of free acid concentration on specific conductivity as a function of temperature is also required for each type of cleaning solution, and an example of this information is shown in FIG. 3.

Based on this information as well as the signals received from probe 41 and titrator 42, the actual free acid concentration of tank 25 is calculated using the algorithm described hereinbefore. If the free acid level has dropped a predetermined percentage below a set point, pump 31 is activated to add concentrated fresh acid into the tank 25. When the acid level is within a predetermined percentage of the desired set point, the pump 31 shuts off.

If the free acid concentration is at a set percentage above the set point, servo-valve 48 is opened and tank 25 is diluted with water from rinse tank 26 until the free acid concentration is again within preset limits. When the level of water in tank 26 decreases, servo-valve 47 opens to replenish tank 26 from second rinse section 13. The water level in tank 27 is replenished by opening of servo-valve 35 and activating pump 34 to supply de-ionized water from tank 33. If the acid concentration is found to be outside the set points, an alarm is activated.

Preferably, the values of free acid, specific conductivity, temperature, bath contamination (total acid free—acid) and offset correction are all logged and displayed by the PLC.

It will be understood that the above detailed description of a cleaning procedure using an acid cleaning solution applies equally well to a cleaning procedure in which the cleaning solution is an alkali solution.

It is also advantageous to provide a conductivity probe in the reservoir 27 of rinse section 13 (Rinse #2), which serves to indicate the degree of contamination of the rinse water. The probe is connected to the PLC 40, which has upper and lower pre-set limits for conductivity. When carry-over into reservoir 27 raises the conductivity above the pre-set upper limit, pump 34 is activated to add de-ionized water. The addition continues until the conductivity is below the lower pre-set limit at which point the pump 34 is stopped.

What is claimed is:

1. A method for automatically controlling a cleaning solution concentration in an aluminum strip cleaning line wherein an aluminum strip is contacted with a chemical cleaning solution while passing through a cleaning bath and the concentration of the chemical in the bath is adjusted by adding either concentrated chemical or water to the bath wherein said chemical is selected from an acid and an alkali and wherein the bath has a free chemical concentration and a total chemical concentration, which method comprises providing a conductivity probe in said cleaning bath and thereby generating a first signal approximately proportional to the free chemical concentration of the bath; providing an on-line process titrator to periodically sample the cleaning bath and by a dual endpoint titrations obtain the free chemical concentration and total chemical concentration of the bath and thereby generate a second signal indicative of an actual free chemical concentration and the total chemical concentration; feeding said first and second signals to a programmable logic controller; based on the signal from the titrator calculating a correction factor for the signal from the conductivity probe to thereby obtain a corrected specific conductivity value for free chemical concentration and adjusting the cleaning bath concentration as required based on the corrected specific conductivity value.

2. A method according to claim 1, wherein the cleaning chemical used is an acid.

3. A method according to claim 2, wherein the bath temperature is measured and a correction factor is applied to the specific conductivity measurement based on the temperature.

4. A method according to claim 2, wherein the specific conductivity is continuously measured.

5. A method according to claim 4, wherein the titrations are conducted at predetermined timed intervals.

6. A method according to claim 2, wherein the acid cleaning solution is sprayed onto top and bottom faces of the aluminum strip by means of spray nozzles arranged above and below the strip.

7. A method according to claim 6, wherein the acid cleaning is followed by at least one water rinse wherein rinse water is sprayed onto the top and bottom faces of the strip.

* * * * *